United States Patent [19]

Lindstrom

[11] Patent Number: 4,781,718
[45] Date of Patent: Nov. 1, 1988

[54] INTRAOCULAR LENS

[76] Inventor: Richard L. Lindstrom, 20050 Lakeview Ave., Excelsior, Minn.

[21] Appl. No.: 106,272

[22] Filed: Oct. 9, 1987

[51] Int. Cl.⁴ .............................................. A61F 2/16
[52] U.S. Cl. ...................................................... 623/6
[58] Field of Search .................... 623/6; 24/297, 17 B, 24/17 AP, 30.5 P

[56] References Cited
U.S. PATENT DOCUMENTS

| | | | |
|---|---|---|---|
| 4,192,022 | 3/1980 | LaHaye | 623/6 |
| 4,551,864 | 11/1985 | Akhavi | 623/6 |
| 4,617,023 | 10/1986 | Peyman | 623/6 |
| 4,642,113 | 2/1987 | Dubroff | 623/6 |

FOREIGN PATENT DOCUMENTS

| | | | |
|---|---|---|---|
| 0227357 | 7/1987 | European Pat. Off. | 623/6 |
| 3130278 | 2/1983 | Fed. Rep. of Germany | 623/6 |

Primary Examiner—Richard J. Apley
Assistant Examiner—James Prizant
Attorney, Agent, or Firm—Hugh D. Jaeger

[57] ABSTRACT

Intraocular lens including loop haptic members each affixed at more than one point to a soft skirt of an optic or to a soft optic for torsional rigidity of the loop haptic member and for preventing loop rotation or pull out in an optic. The loop haptic members each include a main loop haptic member, and two branch members proceeding from the main loop haptic member to affix in securement holes in the edge or surface of an optic. The loops' securement end points include conically shaped end like members which engage within the soft portion of the IOL.

7 Claims, 9 Drawing Sheets

INTRAOCULAR LENS

BACKGROUND OF THE INVENTION

1. Field of the Invention

The present invention relates to an intraocular lens, and more importantly, pertains to a loop haptic member with more than one attachment point to a soft skirt of an optic or to a soft optic.

2. Description of the Prior Art

Prior art loop haptic members in hard or soft lenses often exhibited tendencies to twist in the optic securement holes, or even to disengage entirely by pulling out from the engagement hole, due to lack of attention given to loop securement, resulting in optics which assumed a nonaligned askew position in the chamber of the eye. Often a misaligned loop haptic member would account for tilt of the IOL in the eye.

U.S. Pat. No. 4,642,113 discloses an intraocular lens with fixation filaments being positioned to prevent pupillary capture of the lens body.

The present invention overcomes the disadvantages of the prior art by providing a method of attachment of loop haptic members for IOLs.

SUMMARY OF THE INVENTION

The general purpose of the present invention is an IOL with loop haptic members attached to the optic at more than one point to provide torsional stability and rigidity in soft material of the IOL and provide adequate pullout strength.

According to one embodiment of the present invention, there is provided an optic with two pairs of securement holes for the securement of two loop haptic members therein. Each loop haptic member includes a main loop member, a support member attached, secured or likewise bonded to each main loop member, and a conical anchoring end on the end of each main loop member or support loop member. The conical anchoring ends of the main loop members and the support loop members are somewhat flexible and engage within the securement holes in the optic edge. The diameter of the conical anchoring ends are, by design, slightly larger than the securement holes for compressing or bending inwardly during insertion to allow for a tight and secure engagement fit into the hole. The haptic members secure into either a soft IOL or a soft skirt of an IOL.

One significant aspect and feature of the present invention, is a loop haptic member, or plurality of loop haptic members, which secure at more than one point to the optic to increase torsional rigidity and prevent loop pullout or rotation in soft material of an IOL.

Another significant aspect and feature of the present invention is a conical anchoring end for engagement of a loop haptic member within soft material of an optic or skirt of an IOL.

Having thus described the embodiments of the present invention, it is a principal object hereof to provide a lens which provides torsional rigidity and prevents loop rotation or pullout.

An additional object of the the present invention is to provide a cone shaped anchoring end, thus preventing the possibility of loop pullout.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
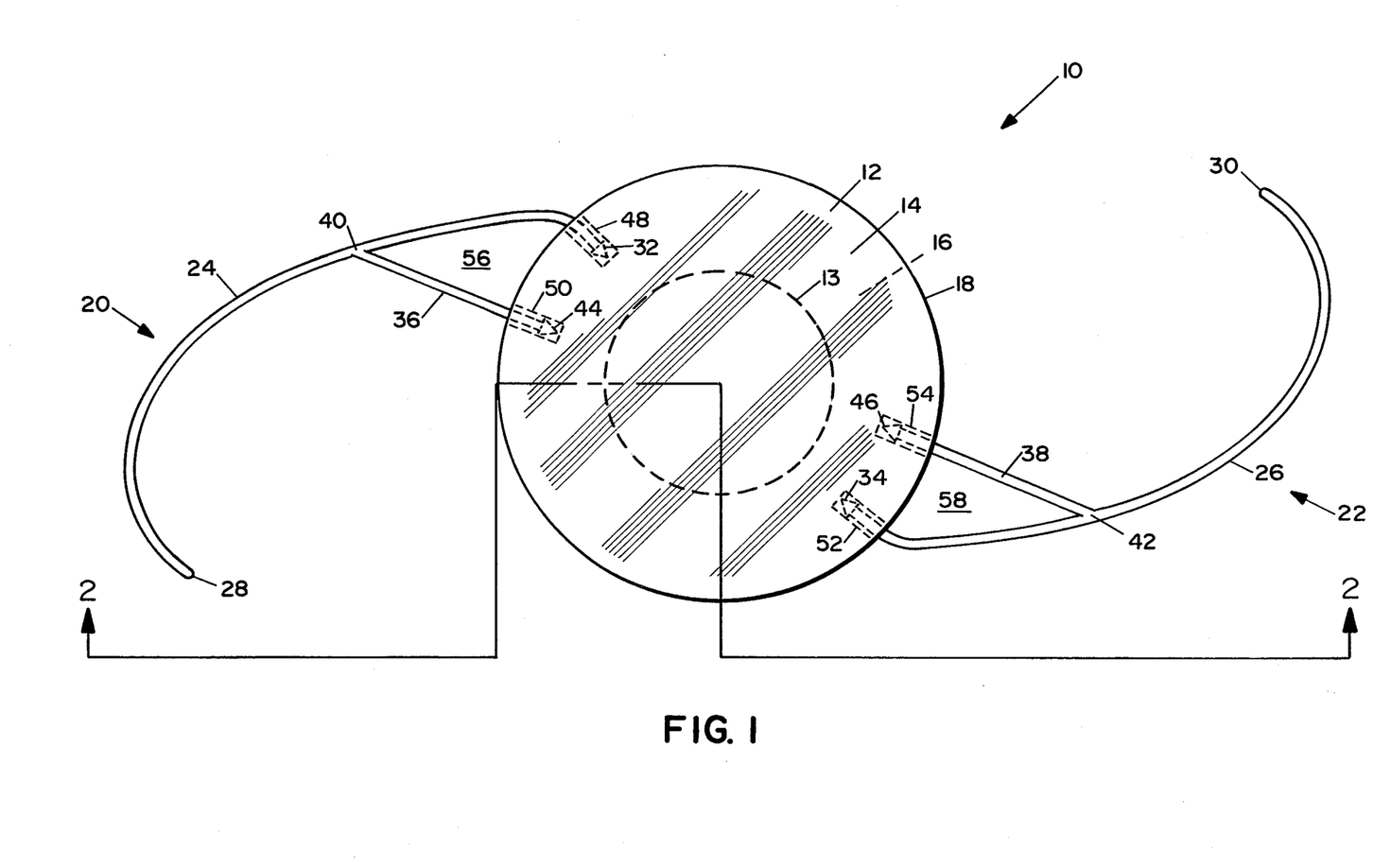
FIG. 1 illustrates a plan view of an intraocular lens with loop haptic members, the present invention.

FIG. 1 illustrates an intraocular lens 10, the present invention, including an optic 12. The optic 12 can be either a soft lens material, such as silicone, hydrogel or the like, or hard lens material 13 as illustrated in dashed lines, such as PMMA or the like with the soft lens material surrounding the optic. The optic 12 includes an upper surface 14, a lower surface 16, and an edge 18 between the upper surface 14 and the lower surface 16. A plano-convex optic is illustrated in this figure; however, the optic can also include other configurations such as a bi-convex optic, meniscus optic, an optic containing a ridge or like barrier or other configurations, and is not to be construed as limiting of the scope of the present invention. Loop haptic members 20 and 22 secure to two or more holes in the optic edge 18. The loop haptic members can be of PMMA or like material. The loop haptic members 20 and 22 include main loop haptic members 24 and 26, respectively; outer tip ends 28 and 30, respectively; conical anchoring ends 32 and 34, respectively; and supporting loop haptic members 36 and 38, respectively, which intersect at junctions 40 and 42, respectively. Supporting loop haptic member 36 includes an anchoring end 44, and the other supporting loop haptic member 38 includes an anchoring end 46. Each of the anchoring ends 32, 34, 44 and 46 are conically shaped, and are slightly larger than the holes 48–54 to assure a positive engagement by flexing of the tip, as later described in detail, when engaged one into the other. The supporting loop haptic members 36 and 38 are ultrasonically welded or by other known methods, joined to the main loop haptic members 24 and 26 at the junctions 40 and 42. The conical anchoring end 44 of the main loop haptic member 24 engages and secures in a securement hole 50. The conical anchoring end 32 of the supporting loop haptic member 36 engages and secures in a securement hole 48. In a like manner, the conical anchoring end 34 of the main loop haptic member 26 engages and secures in a securement hole 52. The conical anchoring end 46 of the supporting loop haptic member 38 engages and secures in a securement hole 54. Securement holes 48, 50, 52 and 54 align perpendicularly to substantial tangents at the intersection of the securement holes 48-54, and can also be angularly aligned. The areas between main loop haptic member 24, supporting loop haptic member 36, optic edge 18; and the area between main loop haptic member 26, supporting loop haptic member 38 and the optic edge 18 are used as positioning holes and are known as positioning areas 56 and 58, respectively. The loop haptic members 20 and 22 are substantially in the same plane as the optic 12, and can also be angled upwardly or downwardly with respect to the optic plane. The loop haptic member can be vaulted or can assume any other configuration with respect to the plane of the optic, and are not considered to be limiting to the scope of the present invention. The loop haptic members 20 and 22 are each secured within the edge 18 of the optic 12 in at least two securement holes, thereby increasing the number of securement engagements by at least twofold to assist in prevention of loop disengagement or pullout from the optic 12. Twisting of the loop haptic members 20 and 22 in the securement holes, and torsional twisting of the loop haptic members 20 and 22, is prevented by the use of at least two securement holes for each loop haptic member.

Figure 2:
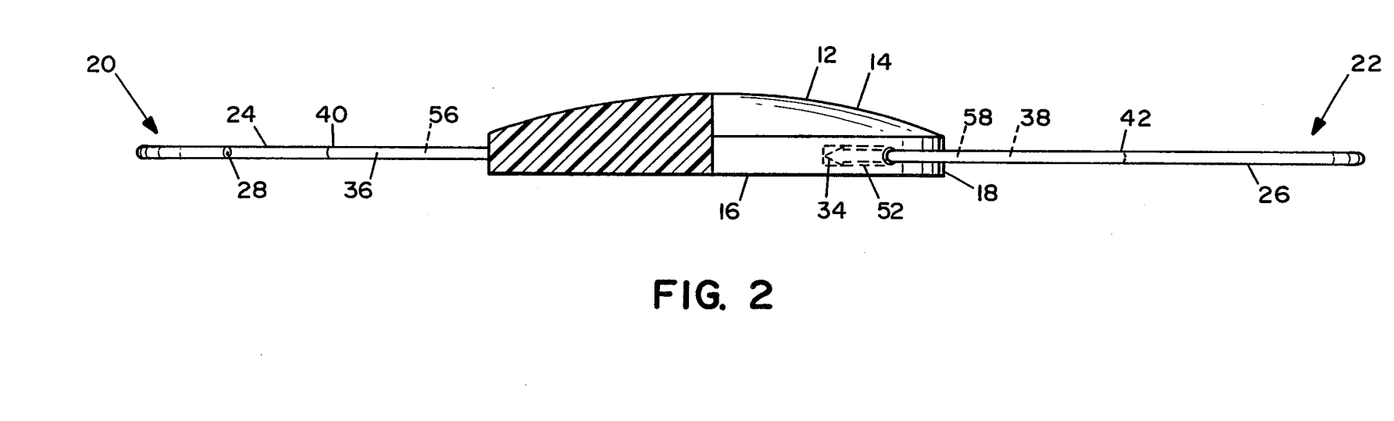
FIG. 2 illustrates a cross-sectional side view of the lens taken along lines 2—2 of FIG. 1.

FIG. 2 illustrates a cross-sectional side view of the lens 10 where all numerals correspond to those elements previously described.

Figure 3:
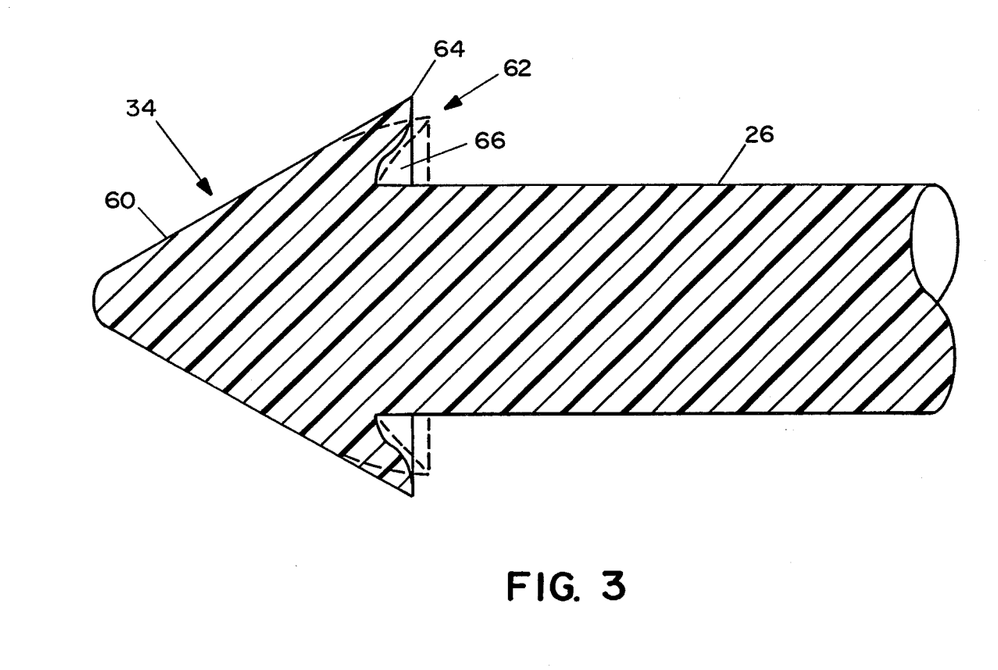
FIG. 3 illustrates an enlarged view of a typical loop conical end.
Figure 4:
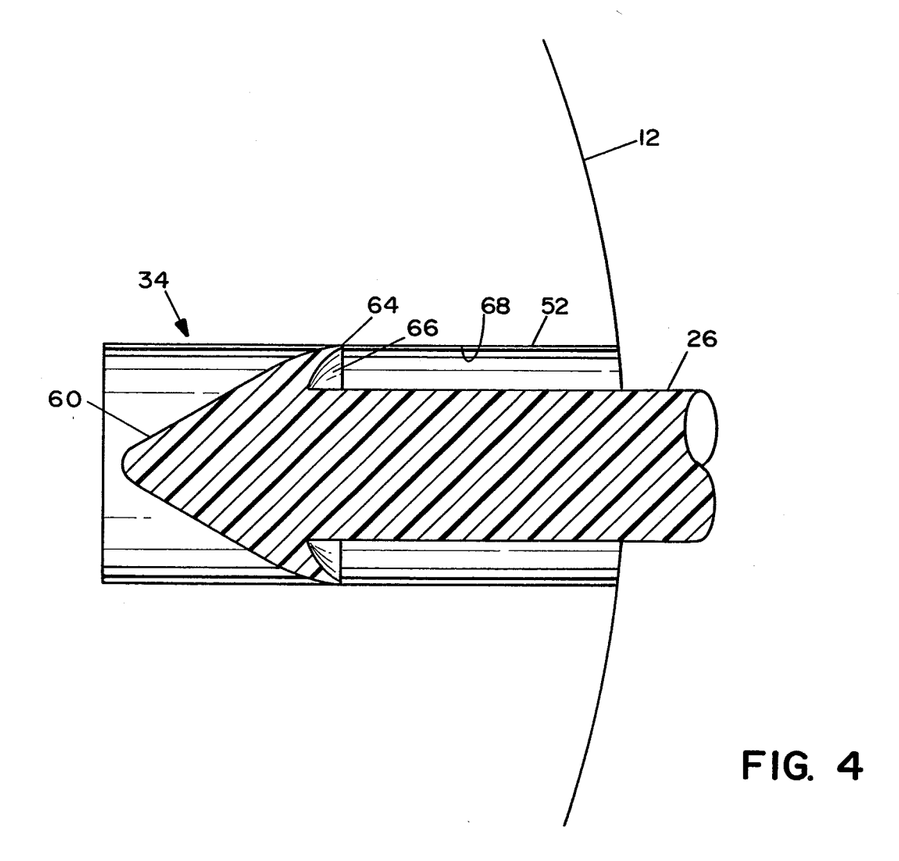
FIG. 4 illustrates a conical end engaged within a securement hole.

FIG. 3 illustrates an enlarged view of a typical loop haptic member conical end, such as conical anchoring end 34, where all numerals correspond to those elements previously described. The conical anchoring end 34 is coaxial with the main or support loop haptic members, and includes a conical surface 60 integral to a loop haptic member, such as the main loop haptic member 26. The base area 62 of the conical anchoring end includes a circular edge 64 and an undercut recess area 66 formed between the circular edge 64 and the main loop haptic member 26. When the conical anchoring end 34 is forceably inserted into a lens securement hole, such as securement hole 52, the undercut recess area 66 allows the circular edge 64 and the material between the circular edge 64 and the undercut recess area 66 to flex inwardly to accommodate the securement hole 54, as shown by dashed lines as illustrated in FIG. 4. The circular edge 64 provides for circular contact of the circular edge in a substantially tangential fashion with the wall 68 of the securement hole 52. Outward spring like qualities of the PMMA or like loop haptic member material assures frictional engagement of the conical anchoring end 34 and the main loop haptic member 26 within the securement hole 52.

FIG. 4 illustrates a conical anchoring end 34 engaged within the securement hole 52 in the optic 12 where the circular edge 64 is compressed and frictionally engaged within the securement hole 52. All other numerals correspond to those elements previously described.

MODE OF OPERATION

The IOL of FIGS. 1-4 is implanted in the posterior chamber by normal IOL implant methods.

ALTERNATIVE EMBODIMENTS

Figure 5:
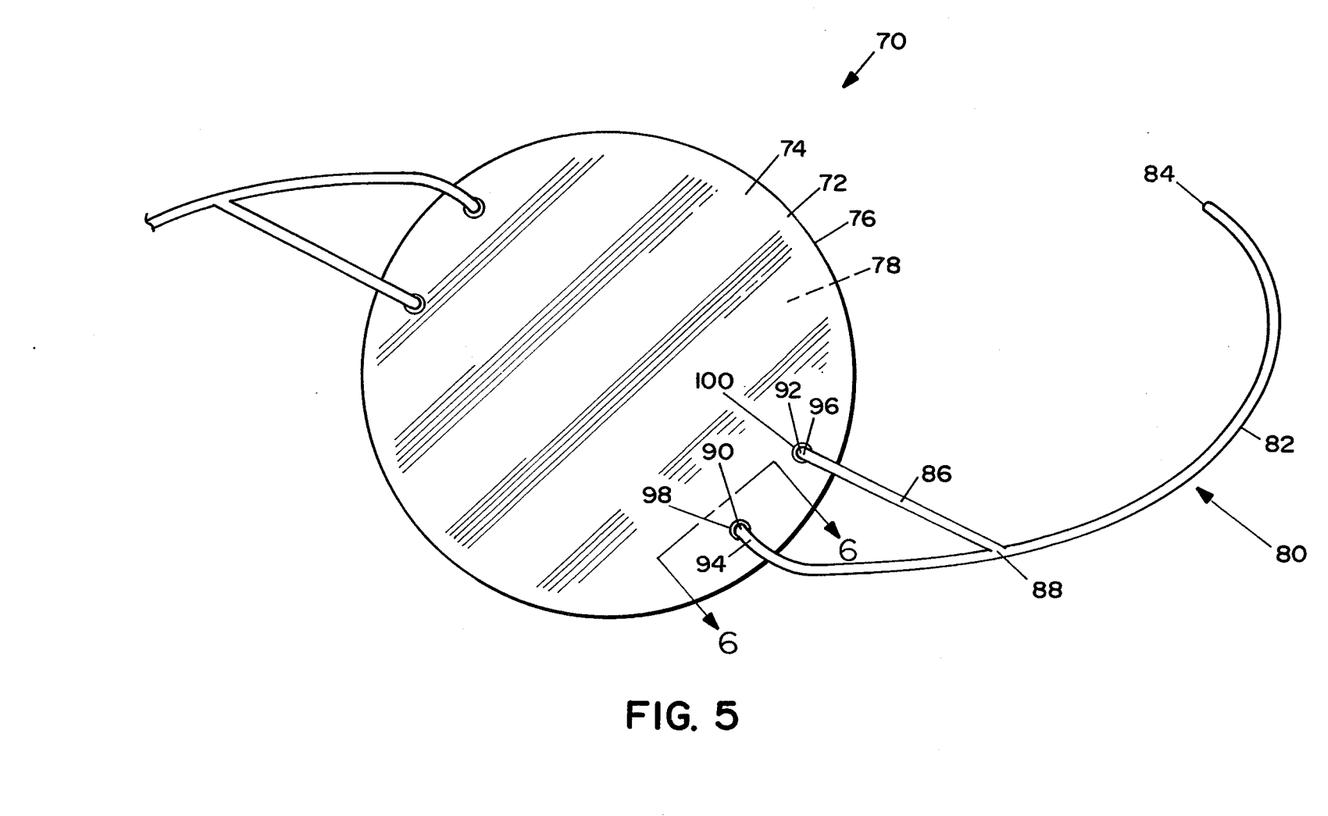
FIG. 5 illustrates an alternative embodiment where the loop haptic members secure into securement holes in the upper surface of a lens.

FIG. 5 illustrates an alternative embodiment of an IOL 70, including an appropriately shaped optic 72 with a top convex surface 74, an edge 76, and a bottom surface 78. One loop haptic member 80 is described for sake of brevity; however, a plurality of loop haptic members can secure to the optic 72. The loop haptic member 80 is very similar to loop haptic member 22, and includes a main loop haptic member 82, loop end 84, a support loop haptic member 86 bonded or affixed to the main loop haptic member at junction 88, and conical loop anchoring ends 90 and 92 on the ends of the main loop haptic member and the support loop haptic member. The inner portions of the main loop haptic member 82 and the support loop haptic member 86 include geometrically configured portions 94 and 96 to allow the conical loop anchoring ends 90 and 92 to enter the optic from the top convex surface 74 through vertically oriented securement holes 98 and 100 instead of through the edge 76. The vertically oriented securement holes 98 and 100 can be substantially perpendicular to the plane of the optic, perpendicular to an upper or lower surface tangent, or can be drilled at any desired angle to the optic.

Figure 6:
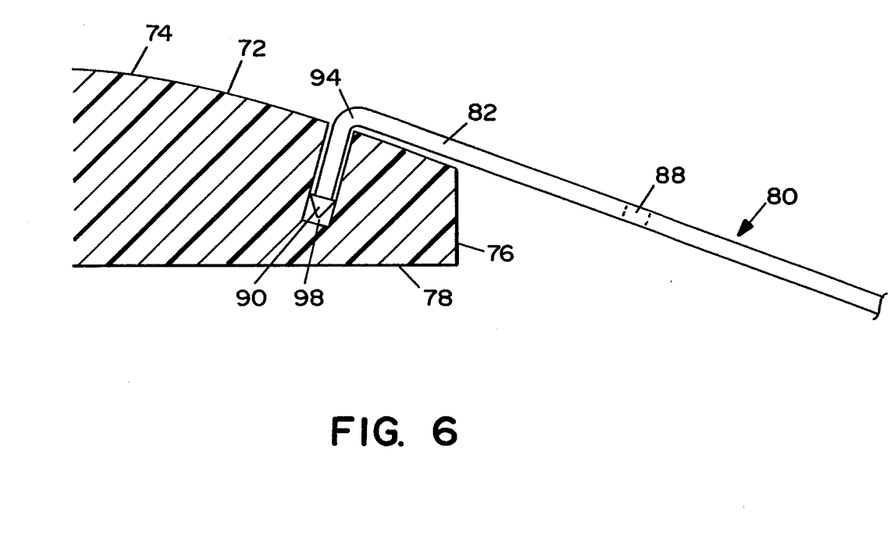
FIG. 6 illustrates a cross-sectional view taken along line 6—6 of FIG. 5.

FIG. 6 illustrates a cross-sectional view of the conical loop anchoring end 90 engaged within a vertically oriented securement hole 98 taken along lines 6—6 of FIG. 5 where all numerals correspond to those elements previously described. The arrangement of the attachment end of a main loop haptic member 82 or a support loop haptic member 86, for all practical purposes, is at substantially right angles to the general plane of loop haptic member 80, and provides a wide degree of security against forces pulling the loop haptic member 80 sideways at an angle of approximately 90° to the axis of the vertically oriented securement hole 98. Torsional rigidity of the loop haptic members are enhanced by this structure, as well as substantially preventing loop rotation or pullout.

Figure 7:
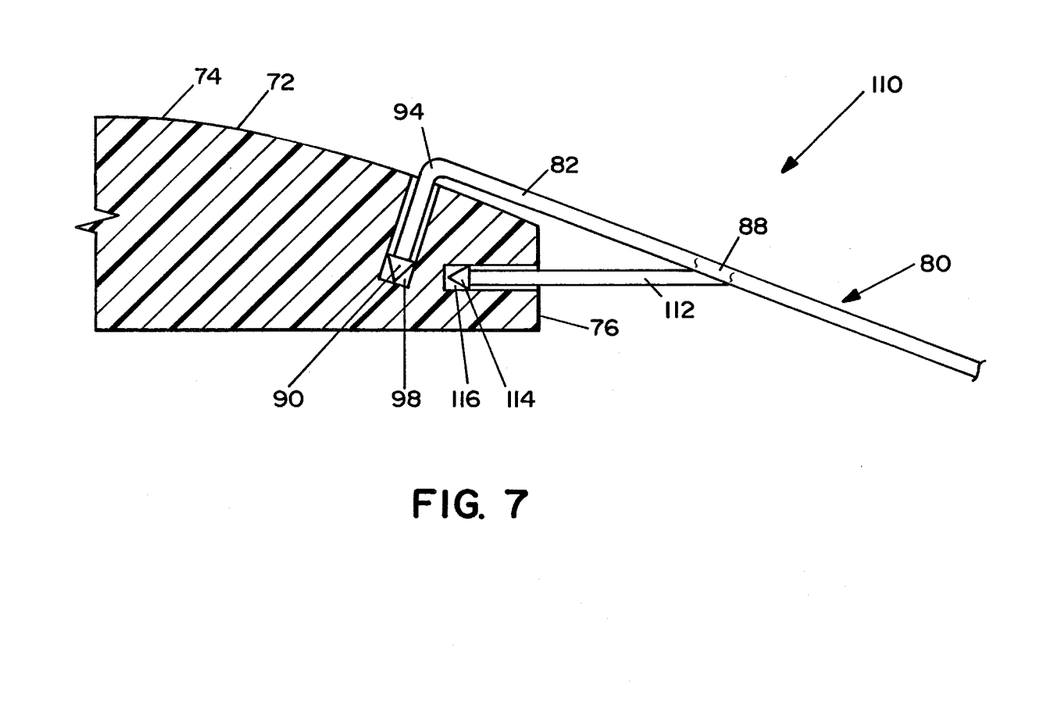
FIG. 7 illustrates a cross-sectional view of a lens where one portion of a loop haptic member secures in a securement hole in the lens top and the support member secures in the optic edge.

FIG. 7 illustrates an alternative embodiment 110 like that of FIG. 6 where all numerals correspond to those elements previously described. A support loop haptic member 112, including a conical anchoring end 114 positions on a securement hole 116 in the edge 76, and the main loop haptic member 82 positions as described in FIG. 8 by offering resistance against loop haptic member pullout and by offering pullout resistance in both the horizontal and the vertical directions to the optic. Torsional rigidity of the loop haptic member is also enhanced, as well as preventing loop rotation or pullout.

In the alternative, a main loop haptic member can secure in a securement hole in the lens edge, and a support loop haptic member can secure in a securement hole in the upper or lower lens surface.

Figure 8:
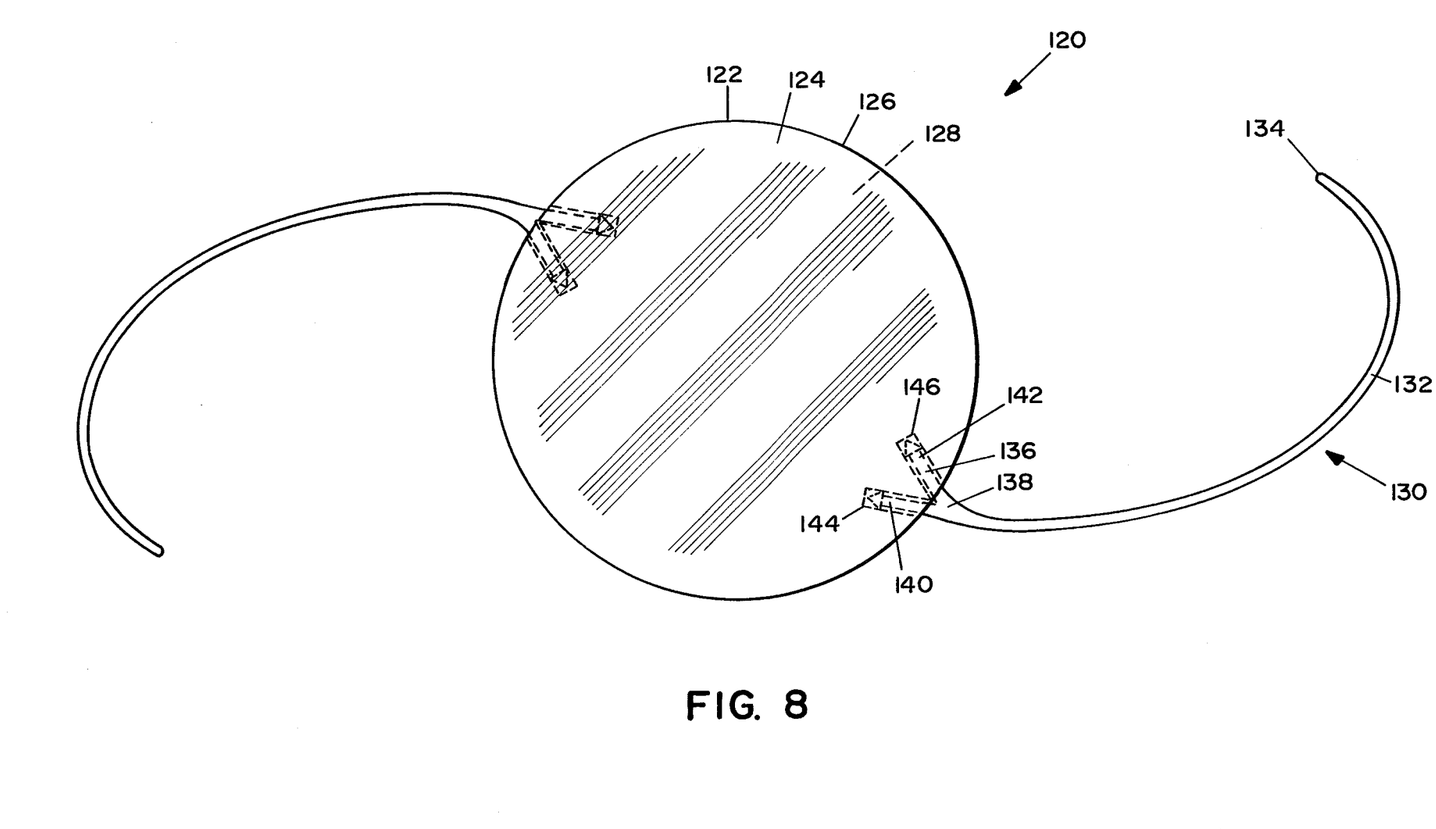
FIG. 8 illustrates an alternative embodiment of an intraocular lens.

FIG. 8 illustrates an alternative embodiment of an IOL 120 including an appropriately shaped optic 122 with a top convex surface 124, an edge 126, and a bottom surface 128. One loop haptic member 130 is described for sake of brevity; however, a plurality of loop haptic members can secure to the optic 122. The loop haptic member 130 includes a main loop haptic member 132, outer loop end 134, a support haptic member 136 bonded or affixed to an angle to the main loop haptic member 132 at junction 138, and conical loop anchoring ends 140 and 142 on the inner end of the main loop haptic member 132 and the support loop haptic member 136, respectively. The conical loop anchoring ends 140 and 142 frictionally engage into holes 144 and 146 in the edge 126 of the optic 122. The conical loop anchoring ends 140 and 142, being frictionally engaged in holes 144 and 146, offer resistance to haptic disengagement from the optic 122, as well as resistance to haptic rotation and misalignment. The angular fixation of the conical loop anchoring ends 140 and 142 to each other also assists to prevent haptic disengagement from the holes 144 and 146 of the optic 122.

Figure 9:
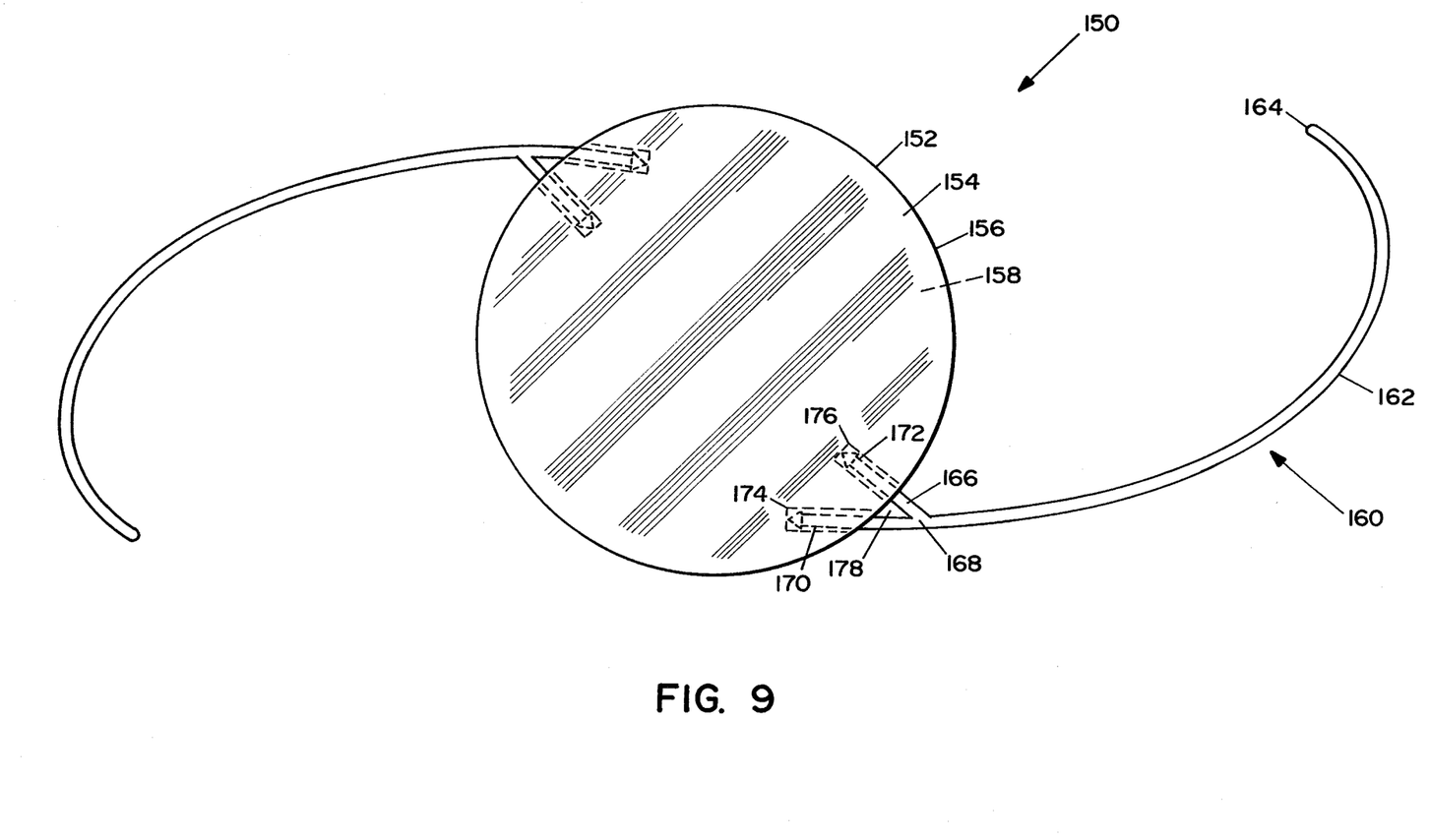
FIG. 9 illustrates an alternative embodiment of an intraocular lens.

FIG. 9 illustrates an alternative embodiment of an IOL 150 including an appropriately shaped optic 152 with a top convex surface 154, an edge 156, and a bottom surface 158. One loop haptic member 160 is described for sake of brevity; however, a plurality of loop haptic members can secure to the optic 152. The loop haptic member 160 includes a main loop haptic member 162, outer loop end 164, a support loop haptic member 166 bonded or affixed to the main loop haptic member 162 at junction 168, and conical loop anchoring ends 170 and 172 on the ends of the main loop haptic member 162 and the support loop haptic member 166, respectively. The conical loop anchoring ends 170 and 172 frictionally engage into holes 174 and 176 in the edge 156 of the optic 152. The holes 174 and 176 are spaced to accommodate the conical loop anchoring ends 170 and 172 which are of sufficient length to allow formation of a triangular like positioning hole 178 formed between the edge 156 of the optic 152 and the portion of the main loop haptic member 162 between junction 168 and hole 174 and also the portion between the support loop haptic member 166 and hole 176. The conical loop anchoring ends 170 and 172, frictionally engaged in holes 174 and 176, offer resistance to haptic disengagement from the optic 152, as well as to haptic rotation and misalignment. The angular fixation of the conical haptic ends 170 and 172 to each other also assists to prevent haptic disengagement from the holes 174 and 176 of the optic 152.

Various modifications can be made to the present invention without departing from the apparent scope thereof.

I claim:

1. An intraocular lens comprising:
    a. an optic; and,
    b. at least one main loop haptic member and at least one supporting loop haptic member, the loop member and the supporting member being joined intermediate their ends, and their proximate ends being immovably secured to the optic by conical barbs on the ends being in tight frictional engagement with the sides of cylindrical bores in the optic.

2. The lens of claim 1 wherein the ends of the haptic members are secured to the optic at its edge.

3. The lens of claim 1 wherein the ends of the haptic members are secured to the optic at its anterior or posterior surface.

4. The lens pf claim 1 wherein the end of one member is secured at the edge of th optic and the end of the other member is secured at the optic's anterior or posterior surface.

5. The lens of claim 1 wherein both members are secured to the edge of the optic and those members and the edge of the optic define an open area.

6. A lens of claim 1 wherein the optic is made of soft material.

7. A lens of claim 1 wherein the optic has a skirt of soft material.

* * * * *